US005874004A

United States Patent [19]

DeWitt

[11] Patent Number: 5,874,004

[45] Date of Patent: Feb. 23, 1999

[54] PHASE SEPARATION FILTER DEVICE

[75] Inventor: Sheila H. DeWitt, Clinton, Mich.

[73] Assignee: Sheila H. DeWitt, Stockton, N.J.

[21] Appl. No.: 666,194

[22] Filed: Jun. 19, 1996

[51] Int. Cl.[6] .......... B01D 11/00

[52] U.S. Cl. .......... 210/634; 210/644; 422/101; 436/177

[58] Field of Search .......... 210/634, 767, 210/487, 489, 474, 455, 660, 644; 422/88, 89, 101; 436/177, 178

[56] References Cited

U.S. PATENT DOCUMENTS

| | | | |
|---|---|---|---|
| 3,295,686 | 1/1967 | Krueger | 210/455 |
| 5,133,934 | 7/1992 | Denton et al. | 422/56 |
| 5,240,680 | 8/1993 | Zuckerman et al. | 422/101 |
| 5,324,483 | 6/1994 | Cody et al. . | |
| 5,464,541 | 11/1995 | Aysta et al. | 210/474 |
| 5,529,694 | 6/1996 | Strickler | 210/634 |

*Primary Examiner*—Ana Fortuna

*Attorney, Agent, or Firm*—Lyon & Artz, PLC

[57] ABSTRACT

An apparatus and method for phase separation of two materials is disclosed. The two materials to be separated are positioned in an extraction cartridge and passed through a filter device, the filter device includes a filter disk member positioned adjacent at least one and preferably two frit members. A drying cartridge may be used to dry the separated liquid material after it leaves the extraction cartridge. The invention can be used for reaction workup, quenching, product isolation and purification.

8 Claims, 1 Drawing Sheet

16
12
34
D2
32
30
20
36
42
10
40
14
50
44

PHASE SEPARATION FILTER DEVICE

TECHNICAL FIELD

The present invention relates to processes and devices for phase separation of materials, particularly for use in multiple, simultaneous synthesis, purification and isolation of compounds.

BACKGROUND ART

Various apparatus and methods are known for the multiple, simultaneous synthesis of compounds, including, but not limited to, organic compounds. Some of the preferred methods and apparatus are shown, for example, in U.S. Pat. No. 5,324,483 entitled "Apparatus for Multiple Simultaneous Synthesis," which is assigned to the same assignee as the present invention. In accordance with that patent, a plurality of compounds are simultaneously synthesized in an array format which is compatible with standard techniques of organic synthesis. The sample handling is carried out using automated systems for speed, accuracy and precision.

The method and apparatus disclosed in the '483 patent can be used for either solid (resin) support or solution based synthesis techniques. The primary steps necessary to perform the synthesis are the development of a synthetic route that will be feasible with the solid or solution techniques utilized, the verification of the synthesis using representative examples, and the execution of the multiple, simultaneous synthesis within an array format to generate the plurality of compounds. The '483 patent increases the flexibility and diversity of structures that can be produced by parallel, solid phase or solution-based chemical synthesis. Where solution-based chemistry is involved, typically two-phase liquid/liquid extraction protocols are utilized. These techniques are not as easily amenable to automation as techniques using solid or resin-support techniques.

SUMMARY OF THE INVENTION

It is an object of the present invention to provide an improved apparatus and method for phase separation. It is also an object of the present invention to provide a phase separation apparatus and method which is useful for multiple, simultaneous synthesis, purification and isolation.

It is a further object of the present invention to provide a two-phase separation apparatus and method which is more amenable to automation and thus which will facilitate a more efficient and faster simultaneous, multiple synthesis, purification and isolation of compounds.

It is still another object of the present invention to provide a phase separation device which is less expensive and easier to manufacture than known separation devices and which also can be provided a disposable form.

These and other objects are met by the present invention which provides an improved apparatus and method for phase separation of different materials. In accordance with the present invention, a hydrophobic paper filter disk is retained on top of or between porous filter devices in the lower end of a phase extraction cartridge. The cartridge has an open end in which the solution or slurry of materials is introduced, often with a solvent, and a lower end which has an outlet for draining and collection of the separated non-hydrophobic materials. Preferably, the separated material is also passed through a drying cartridge attached to or positioned immediately adjacent the exit of the cartridge.

When used for reaction workup and quenching, the crude reaction mixture is introduced into the cartridge containing an aqueous reaction quenching or workup solution, such as water or saturated ammonium chloride. The introduction of additional solvents or reagents to facilitate a two-phase medium is preferred when using aqueous miscible reaction solvents or mixtures. The heavier materials are separated by passing through the frits and hydrophobic paper filter disk, and the separated material is then dried by passing it through the drying cartridge.

These and other features and benefits of the present invention will become apparent when the following description is viewed in accordance with the attached drawings and appended claims.

BEST MODE(S) FOR CARRYING OUT THE INVENTION

The apparatus or device used with the present invention is shown in FIGS. 1–4 and indicated generally by the reference number 10. The device 10 includes an extraction cartridge 12 and a drying cartridge 14. The extraction cartridge 12 is an elongated thin walled container, preferably made from glass or a plastic material. If the extraction cartridge 12 is going to be reused, then preferably it is made from glass or a plastic material such as polypropylene which can be adequately cleaned, sterilized and reused. If the extraction cartridge 12 is disposable, then preferably, it is made from a plastic material such as polyethylene or polypropylene.

Figure 1:
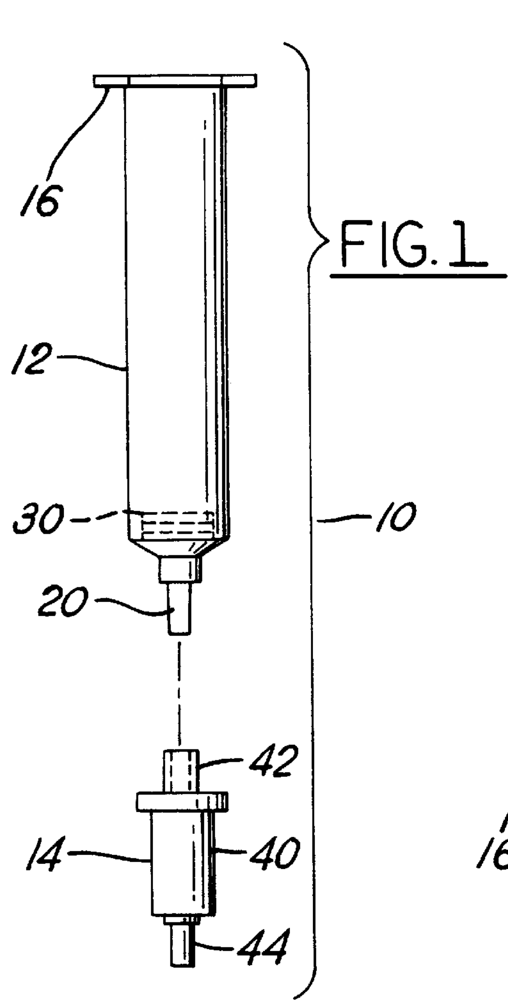
FIG. 1 is an exploded view showing the phase separation cartridge and drying cartridge.
Figure 3:
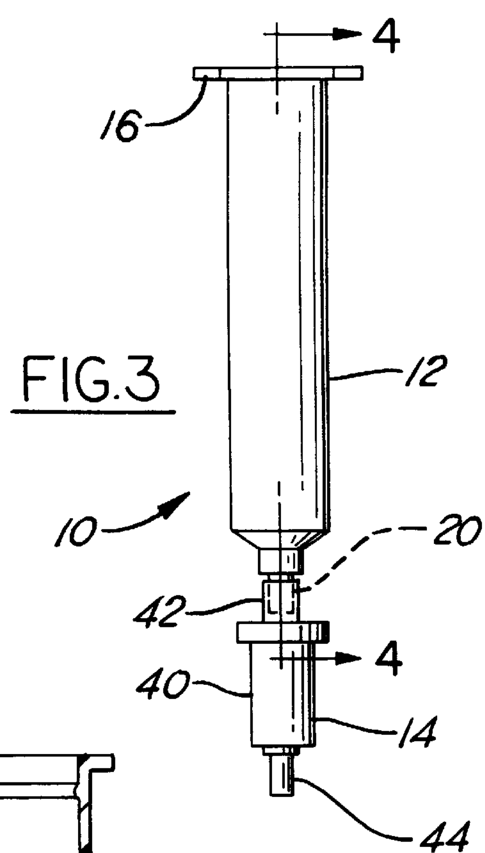
FIG. 3 is a plane view showing the extraction container and drying cartridge assembled together.

The extraction cartridge may have a ledge or lip 16 at its open end to facilitate manual handling and/or automation. The cartridge 12 has a funnel or cone-shaped structure 18 at the opposite end which terminates in a material discharge orifice or outlet 20. The outlet 20 can have any desired shape, but preferably has a tapered shape as shown in FIG. 1 in order to mate with a drying cartridge 14 (as explained below).

Figure 2:
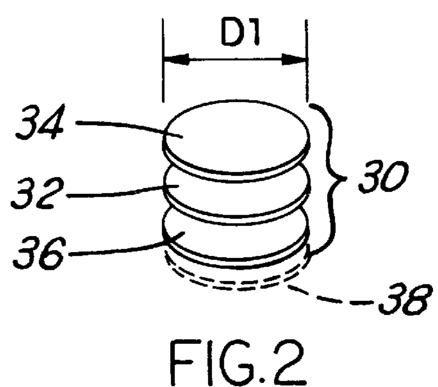
FIG. 2 is an exploded view of the unique filter device.
Figure 4:
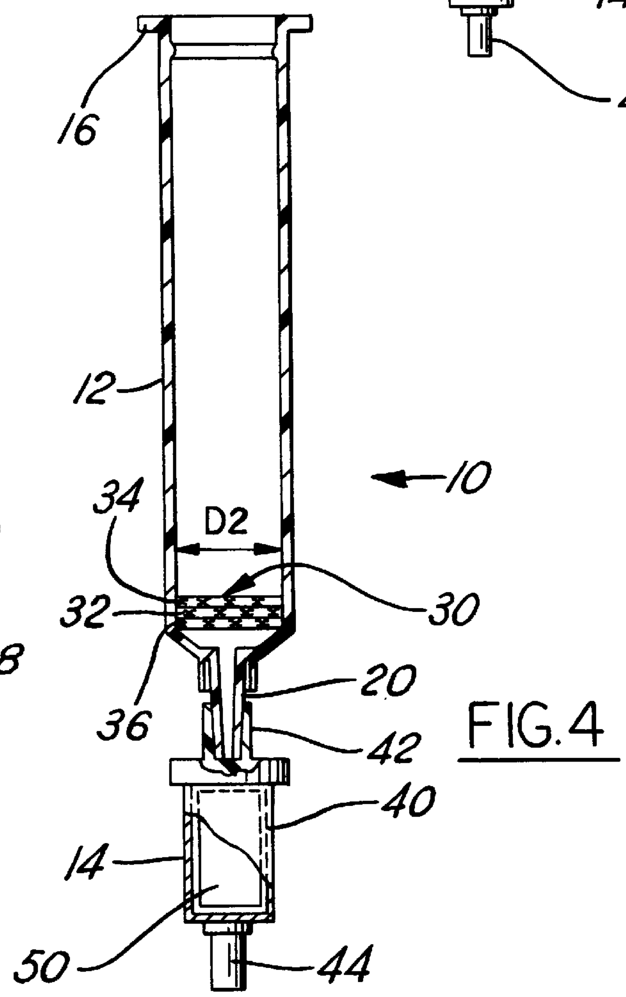
FIG. 4 is a cross-sectional view of the invention shown in FIG. 3, the cross-sectional view being taken along lines 4—4 of FIG. 3 and in the direction of the arrows.

The phase separation mechanism is shown in more detail in FIG. 2 and designated by the reference numeral 30. The phase separation mechanism or apparatus includes a thin circular wafer-like hydrophobic paper disk 32 placed on top of or sandwiched between a pair of thin wafer-like frit members 34 and 36. Preferably, the frit members 34 and 36 are polypropylene frits, but the frit members can be made of any other conventional filtering material, such as Teflon or glass.

The paper filter disk member 32 can be made from any conventional material, but preferably is a silicone treated product, such as the phase separator product from Whatman International, Ltd., Maidstone, England.

Alternatively, another layer, such as a mesh or screen member could be used for reinforcement, if desired. Such a fourth disk member is shown in dotted lines in FIG. 2 and indicated by the reference numeral 38. If desired, as an embodiment, one or more thin wafer-like mesh or screen members could be used in place of the frits 34 and 36.

In use, preferably three layers 32, 34, and 36 are provided and positioned closely together to form a sandwich or laminated type structure. The diameter D1 of the filter device 30 is the same as the inside diameter D2 of the extraction cartridge 12. In this regard, it is preferable that the filter device 30 be sized to contact the inside walls of the extraction cartridge in order to prevent leakage of materials around the device and through the outlet 20.

If only two members are utilized, i.e. one filter disk member 32 and one frit member, then it is preferred that the frit member be positioned below the filter disk member (i.e. on the downstream sides of the filter disk member). Also, it is possible to utilize two or more laminated phase separation mechanisms 30 in the extraction cartridge 12 to insure better separation, although this might slow down the speed of the separation process.

The drying cartridge 14 is also preferably made from a plastic or glass material. The drying cartridge 14 includes a hollow cylindrical body 40, an inlet 42 and an outlet 44. Cartridges of this type are commercially available. Alternatively, a conventional chemical drying material, such as sodium sulfate ($NaSO_4$), which removes residual water from hydrophobic solvents and reagents, may be placed in the body 40. Some conventional drying cartridges use a paper drying member, such as member 50 shown in FIG. 4.

The inlet 42 of the drying cartridge is adapted to mate with the outlet 20 of the extraction cartridge 12. The outlet 44 of the drying cartridge 14 allows the separated material to flow into a collector vessel of some type, such as a beaker or test-tube (not shown) after the separated material is dried by the drying member 50.

If desired, the final separated product could be further purified by conventional means, such as chromatography.

The present invention is an alternative to two-phase liquid/liquid quench and extraction protocols. Solutions of this type from which liquid/liquid extraction protocols include, for example, oil or oil-based materials and water.

The present invention can also be utilized for heavier than water extractions, such as dichloromethane (or $CH_2Cl_2$) (a/k/a methylene chloride and DCM) . DCM is a solvent commonly used in organic synthesis reactions.

An alternative use of the present invention is for the extraction of byproducts from aqueous soluble salts by repeated introduction (and draining) of hydrophobic solvents to the aqueous materials retained in the cartridge. The salts can later be liberated by neutralization and extracted with hydrophibic solvents as described earlier.

The present invention is amenable to automation. This is due to its structure, simplicity, and ease of operation. It is particularly useful for compound workup and separation techniques. For example, for an automated reaction workup, a material, such as a reaction mixture in solution with THF (tetrahydrofuran), can be quenched with, for example, saturated ammonium chloride (sat. $NH_4Cl$), diluted with DCM and extracted. The DCM layer containing the desired product is allowed to separate through the filter device 30 in the extraction cartridge 12. The drying cartridge 14 extracts any water which may be in solution with the dichloromethane thus allowing separation of the dry amine in the DCM.

Initially, the reaction mixture is placed in solution with, for example, tetrohydrofuran (THF) and the mixture is then introduced into the extraction cartridge 12 already containing the saturated ammonium chloride or other quenching material.

An example was carried out utilizing a prototype of the present invention in order to show its usefulness and attributes. The example also demonstrates the ability and invention to be used for parallel processing. In this regard, the phase separation device was used to synthesize and purify imines generated from Grignard reactions.

In this example, a material of 5-nitroanthranilonitrile was dissolved in 1.0 mls of tetrahydrofuran (THF). The two materials were placed in a 10 ml vial. A stir bar and argon blanket were applied. Then, 0.4 ml of 3.0 molar of phenylmagnesium bromide in THC was added to the mixture in the vial. The color change was noted from red to brown to black. An additional 1 ml of THF was added to facilitate stirring.

The reaction was monitored by thin layer chromatography (TLC). After 30 minutes, one-half of the reaction mixture was transferred to a reaction cartridge 12 assembled with a drying cartridge 14 in accordance with the present invention. The reaction was quenched when added to an aqueous solution of saturated ammonium chloride ($NH_4Cl$) already residing in the phase extraction cartridge. DCM was introduced to this mixture to extract the desired product. The phase separation mechanism 30 included two polypropylene frit members 34 and 36, and one silicon treated paper filter disk member 32.

The imine dissolved in DCM and was separated from the material in the extraction cartridge and passed into and through the drying cartridge through outlet 20. The material was collected in a conventional container.

While the best modes for carrying out the invention have been described in detail, those familiar with the art to which this invention relates will recognize various alternative designs and embodiments for practicing the invention as defined by the following claims.

What is claimed is:

1. A method for reaction quench and two-phase liquid/liquid separation comprising the steps of:

a) providing an extraction cartridge, said extraction cartridge comprising an elongated container with a filter mechanism positioned inside, said filter mechanism having a hydrophobic non-absorbing filter disk member positioned adjacent at least one porous supporting member;

b) introducing a reaction mixture into the extraction cartridge container, said reaction mixture having a first liquid material and a second liquid material;

c) quenching said reaction mixture; and d) separating said first liquid material from said second liquid material by passing said first liquid material through said filter device in said extraction cartridge.

2. The method as set forth in claim 1 further comprising the step of drying said first liquid material after it has been separated from said second liquid material.

3. A method as set forth in claim 2 wherein said drying step comprises passing said separated first liquid material through a drying cartridge.

4. A method as set forth in claim 1 wherein said first liquid material is hydrophobic.

5. A method as set forth in claim 4 further comprising the step of drying said first liquid material after it has been separated from said second liquid material.

6. A method as set forth in claim 1 wherein a pair of porous supporting members are provided and said hydrophobic non-absorbing filter disk member is positioned inbetween said porous supporting members.

7. A method as set forth in claim 1 wherein said porous supporting member comprises a frit member.

8. A method as set forth in claim 1 wherein said hydrophobic non-absorbing filter disk member comprises a silicone treated paper material.

* * * * *